United States Patent [19]

Woods et al.

[11] Patent Number: 4,500,359
[45] Date of Patent: Feb. 19, 1985

[54] WAX COMPOSITION USEFUL AS A BEESWAX SUBSTITUTE

[75] Inventors: John H. Woods; Toby R. Graves, both of Longview, Tex.; William E. Nasser, Tulsa, Okla.; Ashvinkumar N. Jagtap, Longview, Tex.

[73] Assignee: Petrolite Corporation, St. Louis, Mo.

[21] Appl. No.: 433,601

[22] Filed: Oct. 8, 1982

Related U.S. Application Data

[63] Continuation of Ser. No. 156,903, Jun. 6, 1980, abandoned.

[51] Int. Cl.$^3$ ............................................. C08L 91/06
[52] U.S. Cl. .................................. 106/270; 106/271; 106/272; 514/285
[58] Field of Search ............... 106/270, 272, 271; 424/365

[56] References Cited

U.S. PATENT DOCUMENTS

| | | | |
|---|---|---|---|
| 2,890,125 | 6/1959 | Mange | 106/23 |
| 3,856,931 | 12/1974 | Fuchs et al. | 424/14 |
| 3,911,105 | 10/1975 | Papantoniou et al. | 424/64 |
| 3,941,608 | 3/1976 | Ehrhardt et al. | 106/285 |
| 4,004,932 | 1/1977 | Bienvenu | 106/31 |

*Primary Examiner*—Alan L. Rotman
*Attorney, Agent, or Firm*—Sidney B. Ring; Leon Zitver

[57] ABSTRACT

This invention relates to a beeswax substitute which comprises a blend of:

(1) an ester of a linear alcohol having at least about 14 carbons and a carboxylic acid or anhydride having at least 2 carbons
(2) an oxidized wax having at least 22 carbons, an
(3) preferably, a fatty acid having at least about 9 carbons;

and to products formed therefrom such as cosmetic emulsions, etc.

18 Claims, No Drawings

WAX COMPOSITION USEFUL AS A BEESWAX SUBSTITUTE

This is a continuation of application Ser. No. 156,903, filed June 6, 1980 now abandoned.

Beeswax is one of the best known of the commercial insect waxes. It has been utilized in various cosmetic formulations for years. Because of its unique properties, beeswax has been found to be especially satisfactory as a major ingredient in numerous formulations.

Although beeswax is generally satisfactory, a great deal of effort has been expended in finding effective substitutes for natural beeswax. An adequate substitute must not only possess properties similar to those of beeswax, but must also exhibit the same properties when formulated into various cosmetic formulations.

The fact that beeswax is available through only a single major source of supply, which, of course, is a secretion of the worker bee, has obviously given impetus to the search for substitutes. At the present, users of the beeswax are concerned about the price which greatly depends upon supply and demand. In addition, the excellent properties of beeswax are to some extent offset by certain disadvantages. In particular, the natural waxes are not always uniform in composition. Thus, it is highly desirable to obtain a synthetic wax composition which is not subject to variations, uncontrollable or otherwise, which would render the natural wax unsuitable for various applications. Also, it would be highly desirable if a synthetic wax composition could be readily and economically obtained, and if the composition had equivalent or superior performance characteristics compared to beeswax.

In the past, many commercial substitutes have been tested, but none has been found to be a full substitute for beeswax.

Accordingly, an object of the present invention is to provide synthetic wax compositions which can replace beeswax in those applications where beeswax is now employed. The chemical composition of beeswax is too highly complex to duplicate it synthetically. Table I shows the chemical composition of yellow beeswax (Ref.—*The Chemistry and Technology of Waxes*, Albin H. Warth, 1956, Page 92. Reinhold Publishing Corporation, New York; Chapman & Hall, Ltd., London.)

TABLE I

| Chemical Composition of Yellow Beeswax | |
|---|---|
| Esters of wax acids | 70.9% |
| Cholesteryl esters of fatty acids | 1.1% |
| Flavones (Coloring matter) | .3% |
| Lactones | .6% |
| Free alcohols | 1–1.25% |
| Free wax acids | 13.5–14.5% |
| Hydrocarbons | 10.5–13.5% |
| Moisture and mineral impurities | 1–2% |
| Physical Properties of Natural Beeswax | |
| Color (ASTM D-1500) | 7.5+ |
| Congealing Point, (ASTM D-938) | 142° F. |
| Melting Point, (ASTM D-127) | 147° F. |
| Penetration, 100/5 @ 77° F. (ASTM D-1321) | 18.5 |
| Acid Number (ASTM D-664) | 20 |
| Saponification Number (ASTM D-94) | 85 |
| Viscosity @ 210° F. (ASTM D-88) | 71 SUS |

We have now discovered a synthetic beeswax which comprises
(I) an ester
(II) an oxidized wax, and, preferably,
(III) a fatty acid.

(I) The Ester

The ester is derived from reacting
(a) an essentially linear alcohol having at least about 14 carbons such as from about 14 to 70 carbons, for example from about 16 to 60 carbons, such as from about 16 to 50 carbons, but preferably from about 18 to 30 carbons, with
(b) an organic acid or equivalent, such as an organic acid anhydride having at least about 2 carbon atoms, such as from about 2 to 33 carbons, for example from about 2 to 20 carbons, such as from about 2 to 5 carbons.

For example, the ester is obtained by reacting an organic acid (monofunctional) such as acetic acid or an anhydride (e.g. acetic anhydride) with an alcohol. Monofunctional acids, useful in the practice of the present invention, are the aliphatic straight chain acids having from 2 to about 33 carbon atoms. Preferably, the monofunctional acid will contain about 2 to 5 carbon atoms; the monofunctional acid containing two carbon atoms being most preferable. Thus, in the practice of the present invention, acetic acid or acetic anhydride is particularly advantageous.

The wax alcohols useful in forming the organic acid esters are those aliphatic alcohols which are available naturally or prepared synthetically using any process. An alcohol used in this invention was prepared by the process of U.S. Pat. No. 2,892,858. Other patents of relevance are U.S. Pat. No. 2,781,419, 2,787,626, 2,826,598, 2,835,689, and British Pat. No. 808,055. The wax alcohol moiety in a polyalkylene group having at least 14 carbons and most preferably from about 16 to 70 carbon atoms. Synthesis involves the following steps.

Triethyl Aluminum Preparation

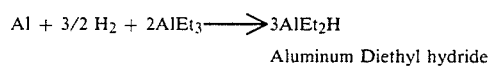

Aluminum Diethyl hydride

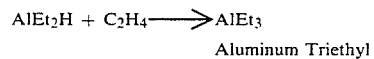

Aluminum Triethyl

Polymerization

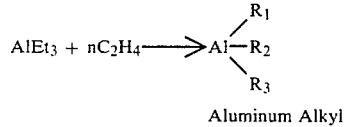

Aluminum Alkyl

Oxidation

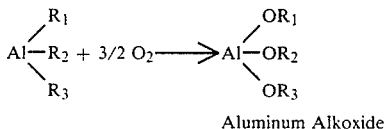

Aluminum Alkoxide

Hydrolysis

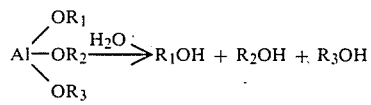

(Reference *Chemical Engineering Progress,* May 1962, page no. 85, Volume 58, No. 5)

These products are essentially linear primary alcohols in the desired carbon range regardless of the method of preparation. All commercial alcohols will contain some branched alcohols and some paraffins. Commercial examples are the ALFOL alcohols as produced by Conoco, and the similar primary alcohols produced by Ethyl Corporation. The commercial examples are mixtures of linear alcohols, branched alcohols and paraffins having an average molecular weight of 210 to 1000. The wax alcohols have a molecular weight of about 210–1000, but preferably from about 300–400, but most preferably about 350, and a melting point (ASTM D-127) of about 120°–195° F., but preferably from about 120°–150° F.

TABLE II

ALFOL 20+ and 22+ Alcohols are mixtures containing high molecular weight, linear primary alcohols in the $C_{20}-C_{28}$ range. They are off white, nearly odorless waxy solids.

| Properties | ALFOL 20+ Typical | ALFOL 22+ Typical |
|---|---|---|
| Total Alcohol, Wt. % | 74 | 65 |
| Wt. % | | |
| (100% Alcohol Basis) | | |
| $C_{18}OH$ and lower | 2 | Tr |
| $C_{20}OH$ and lower | 50 | 5 |
| $C_{22}OH$ | 28 | 50 |
| $C_{24}OH$ | 12 | 26 |
| $C_{26}OH$ | 5 | 11 |
| $C_{28}OH$ and higher | 3 | 8 |
| Hydroxyl Number | 130 | 109 |
| Iodine Number | 12 | 15 |
| Carbonyl, as C=O, Wt. % | 0.3 | 0.4 |
| Water, Wt. % | 0.04 | 0.04 |
| Saponification Number | 6 | 7 |
| Color, Klett (4 cm cell) | 600 | 800 |
| Flash Point, | | |
| Pensky-Martens °F. | 390 | 410 |
| Melting Range, °F. | 45–54 | 45–58 |
| Appearance | Off-White Waxy Solid | Off-White Waxy Solid |

(II) The Oxidized Wax

The oxidized wax is obtained by oxidizing a wax having at least about 22 carbons, such as about 22 to 100 carbons, for example from about 24 to 60 carbons, but preferably from about 28 to 50 carbons. The waxes are, for example, petroleum waxes, (for example microcrystalline, paraffin, etc.), or synthetic waxes such as Fisher-Tropsch wax, alpha-olefins, certain polyolefins, such as polyethylen polypropylene, etc. The oxidized wax stabilizes the paraffinic content of the ester while promoting emulsification.

The preferred oxidized wax is oxidized alpha-olefin.

The oxidized wax has an acid number of at least about 10, such as from about 10 to 50, for example from about 15 to 45, but preferably from about 25 to 35, and a saponification number of at least about 30, such as from about 30 to 100, for example from about 35 to 90, but preferably from about 50 to 70.

Petroleum waxes which are suitable for the purpose of this invention are hard microcrystalline wax, plastic microcrystalline wax, and paraffin wax. The preferred waxes have a melting point within the range of 160°–200° F.

Synthetic hydrocarbon waxes which are applicable in this invention are the intermediate molecular weight polymers, derived from the polymerization and copolymerization, of ethylene, or from the Fisher-Tropsch synthesis of hydrocarbons from carbon monoxide and hydrogen mixtures. Commercially available products typifying the above groups are BARECO POLYWAX 500, POLYWAX 655, and Paraflint wax. The higher molecular weight waxes can be blended with lower molecular weight waxes and other hydrocarbons, such as wax oils, for use in this invention.

Polyethylene of this invention are the various polymers derived from the polymerization of ethylene such as described in U.S. Pat. No. 2,504,400, dated Apr. 18, 1950, U.S. Pat. No. 2,699,457, dated Jan. 11, 1955, Phillips Petroleum Company's Belgian Pat. No. 503,617, dated July 22, 1954, and Kirk-Othmer's *Encyclopedia of Chemical Technology,* Volume 10, PP 938–957. Polypropylenes, polybutylenes, and other olefin polymers and copolymers may also be used in wax blends for the purpose of this invention.

The alpha-olefins referred to in this invention are preferably the straight chain olefins produced by the polymerization of ethylene as described in *Polymerization and Polycondensation Processes,* Advances in Chemistry, Series No. 34 (American Chemical Society, 1962), and by Zeiss, *Organo-Metallic Chemistry* (Reinhold, 1960). The preferred fraction is the $C_{30+}$ alpha-olefin fraction. Lower molecular weight fractions can be used; however, it is advantageous to blend these with higher molecular weight wax.

The art of oxidizing hydrocarbon waxes such as alpha-olefins is well-known and has been extensively described in the literature. The preferred type of oxidation for the purpose of this invention is air oxidation, with or without catalyst, at temperatures ranging from 210° to 420° F. The oxidation of the alpha-olefin should continue until the acid number of about 10 to 50 is obtained. Most preferable in this invention is about 25 to 30+. A commercial example is PETROLITE B-290.

The alpha-olefins employed in this invention are of the following idealized formula $$RCH=CH_2$$

where R is alkyl, for example, having from about 4 to 50 or more carbons. These include monomers such as 1-hexene, 1-octene, 1-decene, 3-methyl decene-1, 1-tetradecene, etc. They may be linear or branched.

Also included within the term alpha-olefin are those which are prepared by polymerizing olefins such as ethylen in the presence of Ziegler type catalysts.

Illustrative of these types of alpha-olefins are those sold by Gulf, for example:

1. Gulf Alpha-Olefin Fraction $C_{20}-C_{24}$ (i.e., mainly $C_{20}-C_{24}$) which contains the following typical carbon distribution:

$C_{18}$: 1 wgt. %
   $C_{20}$: 49
   $C_{22}$: 42
   $C_{24}$: 8
   $C_{26}$: 0.1.

2. Gulf Alpha-Olefin Fraction $C_{24}-C_{28}$ (i.e., mainly $C_{24}-C_{28}$) which contains the following typical carbon distribution:

$C_{22}$: 0.3 wgt. %
   $C_{24}$: 28
   $C_{26}$: 44
   $C_{28}$: 20
   $C_{30+}$: 8.

3. Gulf Alpha-Olefin Fraction $C_{30+}$ (i.e., mostly $C_{30+}$) contains the following typical distribution:

$C_{28}$ and lower: 22 wgt. %
$C_{30}$ and higher: 78.

TABLE III

| | Chevron Chemical Co. | | | | | |
|---|---|---|---|---|---|---|
| | CARBON RANGE | | | | | |
| | $C_6-C_9$ | $C_{10}$ | $C_{11}-C_{14}$ | $C_{15}-C_{18}$ | $C_{18}-C_{20}$ | $C_{15}-C_{20}$ |
| Straight Chain Mono Alpha-Olefins, Wt. % | 89 | 90 | 89 | 91 | 86 | 88 |
| Diolefins, Wt. % | 4 | 5 | 6 | 8 | 4 | 5 |
| Paraffins, Wt. % | 3 | 2 | 1 | 2 | 9 | 5 |
| Appearance | Clear and bright and free of sediment | | | | | |
| Color, Saybolt | +18 | +17 | +14 | +7 | −16 | −12 |
| Density (20°/4° C.) g/ml | 0.713 | 0.751 | 0.770 | 0.783 | 0.797 | 0.787 |
| Density (60°/60° F.) lb/gal | 5.95 | 6.27 | 6.42 | 6.57 | 6.68 | 6.60 |
| Flash Point, TOC, °F. | 30 | 103 | 162 | 260 | 330 | 280 |
| Pour Point, °F. | — | — | −20 | +40 | +70 | +55 |
| Bromine No. g/100 g | 165 | 118 | 98 | 73 | 57 | 67 |
| Water Content, ppm | 130 | 130 | 130 | 80 | 40 | 50 |
| Sulfur Content, ppm | 5 | 8 | 10 | 15 | 15 | 15 |
| Carbon Number Distribution, Wt. % | | | | | | |
| $C_5$ | 2 | | | | | |
| $C_6$ | 39 | | | | | |
| $C_7$ | 24 | | | | | |
| $C_8$ | 17 | | | | | |
| $C_9$ | 16 | 4 | | | | |
| $C_{10}$ | 2 | 15 | 1 | | | |
| $C_{11}$ | | 1 | 27 | | | |
| $C_{12}$ | | | 24 | | | |
| $C_{13}$ | | | 24 | | | |
| $C_{14}$ | | | 23 | 1 | | 1 |
| $C_{15}$ | | | 1 | 29 | | 17 |
| $C_{16}$ | | | | 28 | | 18 |
| $C_{17}$ | | | | 27 | 1 | 17 |
| $C_{18}$ | | | | 14 | 23 | 17 |
| $C_{19}$ | | | | 1 | 37 | 15 |
| $C_{20}$ | | | | | 30 | 12 |
| $C_{21}$ | | | | | 9 | 3 |
| Average Molecular Weight | 100 | 140 | 174 | 228 | 269 | 244 |

Other alpha-olefins can also be employed individually, in combination, or as components of commercial raw materials.

The term alpha-olefins as employed herein relates primarily to alpha-olefins of the formula $RCH=CH_2$ but does not exclude alpha-olefins of the vinylidene structure.

(III) The Fatty Acid

The fatty acid has at least about 9 carbons, such as from about 9 to 33 carbons, for example from about 12 to 30 carbons, but preferably from about 16 to 24 carbons.

They have acid numbers of at least about 110, such as about 110 to 400, for example from about 130 to 300, but preferably from about 150 to 200.

Preferred examples of fatty acids include stearic acid ($C_{17}H_{35}COOH$), nondecyl acid ($C_{18}H_{37}COOH$), arachidic acid ($C_{19}H_{39}COOH$) or behenic acid. A commercial example of behenic acid is Humko Sheffield's Hystrene 9022.

The following Table illustrates suitable fatty acids.

TABLE IV

| A. | Saturated | $C_nH_{2n+1}COOH$ or $C_nN_{2n}O_3$ |
|---|---|---|
| | pelargonic acid | $C_8H_{17}COOH$ |
| | capric acid | $C_9H_{19}COOH$ |
| | undecylic acid | $C_{10}H_{21}COOH$ |
| | lauric acid | $C_{11}H_{23}COOH$ |
| | tridecoic acid | $C_{12}H_{25}COOH$ |

TABLE IV-continued

| | myristic acid | $C_{13}H_{27}COOH$ |
|---|---|---|
| | pentadecanoic acid | $C_{14}H_{29}COOH$ |
| | palmitic acid | $C_{15}H_{31}COOH$ |
| | margaric acid | $C_{16}H_{33}COOH$ |
| | stearic acid | $C_{17}H_{35}COOH$ |
| | nondecylic acid | $C_{18}H_{37}COOH$ |
| | arachidic acid | $C_{19}H_{39}COOH$ |
| | behenic acid | $C_{21}H_{43}COOH$ |
| | carnaubic acid | $C_{23}H_{47}COOH$ |
| | hyenic acid | $C_{24}H_{49}COOH$ |
| | carboceric acid | $C_{25}H_{51}COOH$ |
| | cerotic acid | $C_{26}H_{53}COOH$ |
| | lacceroic acid | $C_{31}H_{63}COOH$ |
| | melissic acid | $C_{29}H_{59}COOH$ |
| | montanic acid | $C_{28}H_{57}COOH$ |
| | psyllic acid | $C_{32}H_{65}COOH$ |
| B. | Unsaturated such as oleic, etc. | $C_nH_{2n-1}COOH$ or $C_nH_{2n-2}O_2$ |
| C. | Unsaturated | $C_nH_{2n-3}COOH$ or $C_nH_{2n-4}O_2$ |
| | sorbic acid | $C_5H_7COOH$ |
| | linoleic acid | $C_{17}H_{31}COOH$ |
| D. | Unsaturated linolinic acid | $C_nH_{2n-5}COOH$ or $C_nH_{2n-5}O$ $C_{17}H_{29}COOH$. |

The compositions of this invention include the following components having the properties indicated.

TABLE V

| Wax Alcohol Esters | Broad Range (about) | Intermediate Range (about) | Preferred Range (about) |
|---|---|---|---|
| C.P. (D-938) °F. | 95–180 | 100–150 | 105–115 |
| M.P. (D-127) °F. | 95–180 | 100–160 | 105–120 |

TABLE V-continued

| Wax Alcohol Esters | Broad Range (about) | Intermediate Range (about) | Preferred Range (about) |
| --- | --- | --- | --- |
| Vis @ 210° F. (D-88) (SUS) | 20–200 | 25–150 | 30–60 |
| Acid No. (D-664) | 0–5 | 0–3 | 0–2 |
| Sap. No. (D-94) | 50–210 | 70–180 | 90–120 |

TABLE VI

| Oxidized Waxes | Broad Range (about) | Intermediate Range (about) | Preferred Range (about) |
| --- | --- | --- | --- |
| C.P. (D-938) °F. | 120–210 | 130–180 | 140–160 |
| M.P. (D-127) °F. | 120–220 | 135–200 | 150–180 |
| Vis @ 210° F. (D-88) (SUS) | 40–200 | 60–160 | 85–120 |
| Pen. @ 77° F. (D-1321) (dmm) | 1–80 | 4–30 | 10–20 |
| Acid No. 77° F. (D-1321) (dmm) | 10–50 | 15–45 | 25–35 |
| Sap. No. (D-94) | 30–100 | 35–90 | 50–70 |

TABLE VII

| Beeswax Substitutes Product of this invention | Broad Range (about) | Intermediate Range (about) | Preferred Range (about) |
| --- | --- | --- | --- |
| C.P. (D-938) °F. | 95–210 | 105–180 | 115–150 |
| M.P. (D-127) °F. | 100–220 | 120–200 | 140–100 |
| Pen. @ 77° F. (D-1321) (dmm) | 2–100 | 3–75 | 4–50 |
| Vis. @ 210° F. (D-88) (SUS) | 20–200 | 25–150 | 30–100 |
| Acid No. (D 664) | 5–80 | 10–60 | 15–30 |
| Sap. No. (D-94) | 50–200 | 75–160 | 100–130 |

The following examples are presented for purposes of illustration and not of limitation.

Example I

Preparation of an ester using $C_{22+}$ ALFOL from Conoco and acetic anhydride: A one liter, three necked flask was charged with 400 grams of $C_{22+}$ ALFOL (0.86 moles of hydroxyl group) which was melted and the temperature adjusted to 220° F. 87.7 grams of acetic anhydride (0.86 moles) was added to the ALFOL in the reaction. The mixture was reacted while stirring for 2 hours and 15 minutes, at 220°–230° F. The temperature was increased to 300° F. and a full vacuum (about 30 inches of Hg) was applied for 2 hours. The product had an acid value of 1 and a saponification value of 97.

Physical Properties for Ester

| C.P. (ASTM D-928) | 109° F. |
| --- | --- |
| M.P. (D-127) | 112° F. |
| Vis. @ 210° F. (ASTM D-88) | 37.0 SUS |
| Acid # (ASTM D-664) | 1 |
| Sap. # (ASTM D-94) | 97 |

EXAMPLE II

Oxodation of $C_{30+}$ alpha-olefin: 1000 grams of a $C_{30+}$ alpha-olefin from Gulf, having a melting point of 160°–175° F., was charged into a vessel. The wax was blown with air until the product showed an acid number of 30. This oxidation requires approximately 26 hours to achieve the desired acid number, depending upon the temperature and the degree of dispersion of the air. The following analysis was obtained on the final product:

| C.P. (D-938) | 150° F. |
| --- | --- |
| M.P. (D-127) | 168° F. |
| Vis. @ 210° F. (D-88) | 115.5 SUS |
| Color (D-1500) | 1.5 |
| Pen @ 77° F. (D-1321) | 15 |
| Acid # (D-664) | 30 |
| Sap # (D-94) | 76 |

EXAMPLE III

Preparation of Wax Blend 70.8 parts of organic ester of Example I was melted and blended with 19.5 parts of oxidized $C_{30+}$ alpha-olefin of Example II and 9.7 parts of Behenic acid (Humko Sheffield's Hystrene 9022). The resulting smooth and uniform composition had the following properties:

| C.P. (D-938) | 118° F. |
| --- | --- |
| M.P. (D-127) | 159° F. |
| Vis. @ 210° F. (D-88) | 43.0 SUS |
| Color (D-1500) | 2.5 |
| Pen @ 77° F. (D-1321) | 42.5 |
| Acid # (D-664) | 23 |
| Sap # (D-94) | 115 |

EXAMPLE IV

A cosmetic cream was prepared from the wax blend of Example III as follows.

Oil Phase:
11 parts of wax blend of Example II
6 parts paraffin
Examples VI, VII and VIII, which follow, have no oxidized wax and are for comparative purposes only.
Water Phase:
34 parts deionized water
1 part Borax Both phases were heated to 167° F. with slow agitation. The water phase was added to the oil phase with fast agitation. The cream was cooled to room temperature. The resulting cream had excellent stability, gloss, and a smooth texture, and was comparable to an identical emulsion prepared with natural beeswax.

EXAMPLE V

A cream prepared from Example IV was placed in the oven at 106° F., along with the cream made from natural beeswax for 6 weeks. The stability of the cream from Example IV was found to be very similar to the stability of the cream made from beeswax.

The following example has no oxidized wax.

EXAMPLE VI 19.5 parts of unoxidized $C_{30+}$ alpha-olefin was substituted for oxidized $C_{30+}$ alpha-olefin in the wax composition of Example III. An appreciable difference in the wax composition was observed. A borax employing the wax gave a very poor emulsion from which two phases separated.

EXAMPLE VII

An extra 6.5 parts of Behenic acid was added to the wax composition of Example VI. A borax emulsion employing the wax composition gave a grainy and unstable emulsion.

From Examples VI and VII which contain no oxidized wax, it is noticeable that the wax composition of the present invention containing oxidized wax, has very unique properties, which are very similar to that of natural beeswax.

EXAMPLE VIII 19.5 parts of Carnauba was substituted for the ozidized $C_{30+}$ alpha-olefin in the wax composition of Example III. Oil retention properties of the wax composition were improved, but the borax emulsion incorporating the wax had a rough texture. The emulsion separated after aging two days at 106° F. The following physical properties were obtained for this wax composition:

| | |
|---|---|
| C.P. (D-938) | 155° F. |
| M.P. (D-127) | 165° F. |
| Pen. 100/5 @ 77° F. (D-1321) | 22 |
| Acid # (D-664) | 20 |
| Sap # (D-94) | 102 |
| Vis. @ 210° F. (D-88) | 47.2 SUS |
| Color (D-1500) | 2. |

The following example illustrates the oxidation of a wax blend other than alpha-olefin.

EXAMPLE IX

A blend consisting of 50% PETROLITE C-700 wax (a tank bottom derived microcrystalline wax with a melting point of typically 196° F.) and 50% BARECO POLYWAX-655 (a synthetic wax, typically 210° F. melting point) was charged to an oxidizer. The wax was oxidized to 32 acid number (75 saponification number). Physical properties of the oxidized blend are listed below:

| | |
|---|---|
| C.P. (D-938) | 174° F. |
| M.P. (D-127) | 195° F. |
| Pen. 100/5 @ 77° F. (D-1321) | 6.4 |
| Acid # (D-664) | 32 |
| Sap # (D-94) | 76 |
| Vis. @ 210° F. (D-88) | 190.6 SUS |
| Color (D-1500) | 2.5. |

EXAMPLE X 19.5 parts of oxidized wax from Example IX was substituted for the oxidized $C_{30+}$ alpha-olefin in the wax composition of Example III. The wax composition has good oil retention property at 106° F. The borax emulsion, as described in Example IV, gave a good, textured cream, very similar to the cream using natural beeswax. Physical properties are listed below:

| | |
|---|---|
| C.P. (D-938) | 140° F. |
| M.P. (D-172) | 147° F. |
| Pen. 100/5 @ 77° F. (D-1321) | 43.5 |
| Acid # (D-664) | 23 |
| Sap # (D-94) | 98 |
| Vis. @ 210° F. (D-88) | 47.5 SUS |
| Color (D-1500) | 3.5. |

EXAMPLE XI

The wax composition of Example III was employed in the following cream formulations where beeswax is typically employed.

| Emollient Cream | |
|---|---|
| | Grams |
| Oil Phase | |
| Isopropyl Isostearate | 5.00 |
| Isopropyl Myristate | 5.00 |
| Stearic Acid, USP | 9.00 |
| Wax Blend of Example III | 3.00 |
| Lanolin Oil | 3.00 |
| Mineral Oil, 70 Viscosity | 10.00 |
| Propyl Paraben | 0.03 |
| Sorbitan Monostearate | 1.00 |
| Water Phase | |
| PEG-600 Monoisostearate | 2.00 |
| Glycerine CP/USP (99.5%) | 8.10 |
| Triethanolamine | 1.80 |
| Deionized Water | 51.00 |
| Methyl Paraben | 0.07 |

Procedure: Both the phases were heated to 167° F. with slow agitation. The water phase was added to the oil phase with slow agitation. The cream was cooled with slow agitation.

| | Cleansing Creams | |
|---|---|---|
| | I | II |
| Formula No. | Grams | Grams |
| Oil Phase | | |
| Wax Blend of Example III | 14.00 | 7.00 |
| Paraffin | 14.00 | — |
| Lanolin, USP, Anhydrous | 3.00 | 5.00 |
| Tween 60 | 2.00 | — |
| Mineral Oil | 32.00 | 50.00 |
| Propyl Paraben | 0.10 | 0.07 |
| Water Phase | | |
| Deionized Water | 33.70 | 36.73 |
| Borax | 1.00 | 1.00 |
| Methyl Paraben | 0.20 | 0.20 |

Procedure: Both the phases were heated to 167° F. with slow agitation. Then the water phase was added to the oil phase with fast agitation. The resulting cream was cooled to 73.4° F. with agitation.

The resulting emollient cream was soft and had a very good texture. Both the cleansing creams and the emollient cream had superb gloss and a smooth texture. All of the emulsions exhibited excellent stability, gloss, and texture.

In summary, the wax composition of Example III, which contains oxidized $C_{30+}$ alpha-olefin, shows three important characteristics: (1) good oil binding property, (2) superb emulsification in the cleansing cream formulation of Example IV, and (3) the similarity of the melting point characteristic with the natural beeswax, which suits all the applications where beeswax is presently employed.

All the three characteristics achieved in this invention are greatly increased due to the oxidized wax. The oxidized wax has a very good binding power for oil. The following Table VIII illustrates the effect of different oil binders on emulsifications.

TABLE VIII

| Kind of wax blended as an oil binder in the composition | Oil Retention | Borax Emulsion (Example IV Type) | Thermal Stability of the Emulsion at 106° F. |
|---|---|---|---|
| Oxidized $C_{30+}$ Alpha-Olefin | Good | Excellent | Excellent |
| Oxidized Wax (50% microcrystalline wax 50% polyethylene wax) | Very Good | Good | Good |
| Carnauba | Excellent | Fair | Separated |
| $C_{30+}$ Alpha-Olefin (unoxidized) | Fair | Separated | Separated |
| BARECO POLYWAX-655 (unoxidized) | Fair | Very Grainy | Separated |

In summary, the composition of this invention comprises an ester, an oxidized wax, and preferably a fatty acid.

The first ingredient is an ester, obtained by reacting an essentially linear alcohol having at least about 14 carbons such as about 14 to about 70 carbon atoms and an organic acid or organic anhydride having from at least about 2 carbons, as about 2 to about 33 carbon atoms.

The second ingredient is an oxidized wax having at least about 22 carbons, such as about 22 to about 100 carbon atoms and which will have an acid value at least about 10, such as from about 10 to about 50, and a saponification value from at least about 30, such as about 30 to about 100.

The third consitutent of the present invention is the fatty acid having at least about 9 carbons, such as about 9 to about 33 carbon atoms, such as stearic or behenic acid and having acid numbers from at least about 110, such as about 110 to about 400.

All three described constituents are blended together to get a final acid number from at least about 5, such as about 5 to about 50 and a saponification number from at least about 50, such as about 70 to about 210, for example from about 75 to 160, but preferably from about 90 to 150 with an optimum of about 100 to 130.

The properties of the synthetic beeswax of this invention can vary widely depending on the specific components, the ratios thereof, etc. In general, as a weight percentage of the total blend, the composition may comprise:

| Component | Broad Range (about) | Intermediate Range (about) | Preferred Range (about) | Optimum Range (about) |
|---|---|---|---|---|
| Ester | 40–90% | 60–80% | 65–80% | 70–75% |
| Oxidized wax | 5–50% | 10–30% | 12–25% | 15–20% |
| Fatty acid | 0–40% | 5–30% | 5–20% | 8–15% |

We claim:

1. A wax composition useful as a beeswax substitute comprising (1) 40–90% by weight of a wax alcohol ester whose alcohol moiety is a linear polyalkylene group of about 4 to 70 carbons and whose acid moiety is that of a monofunctional straight chain carboxylic acid of from 2 to about 33 carbon atoms, said wax alcohol ester having an acid number of 0.5 and a melting point of 95° to 180° C. and (2) 5–50% by weight of an oxidized hydrocarbon wax of about 22–100 carbons.

2. A wax composition of claim 1 which also contains (3) up to 40% by weight of a fatty acid of 9–33 carbons.

3. The composition of claim 1 where the alcohol moiety of the ester (1) has about 18 to 30 carbons and the acid moiety of said ester (1) has about 2 to 5 carbons; the oxidized wax (2) has from about 28 to 50 carbons; and the fatty acid (3) has about 16 to 24 carbons.

4. The composition of claim 3 where the ester (1) is from 65–80%, the oxidized wax (2) is about 12–25% and the fatty acid (3) is from 5 to 20%, all % by weight, of the total composition.

5. The composition of claim 2 where the oxidized wax (2) has an acid number of about 10 to 50 and a saponification number of about 30 to 100.

6. The composition of claim 5 where the alcohol moiety of the ester (1) is at least a $C_{18+}$ linear polyalkylene group and the oxidized wax (2) is an oxidized alpha-olefin, Fischer-Tropsch, poly-olefin, or microcrystalline wax, or a mixture thereof, and the fatty acid (3) has from about 16 to 30 carbons.

7. The composition of claim 2 having a melting range of from about 100°–220° F., an acid number of about 5–50, and a saponification number of about 70–210.

8. The composition of claim 6 having a melting range of from about 130°–175° F., an acid number of about 5–50, and a saponification number of about 70–210.

9. A cosmetic emulsion of the composition of claim 1.

10. A cosmetic emulsion of the composition of claim 2.

11. A cosmetic emulsion of the composition of claim 3.

12. A cosmetic emulsion of the composition of claim 4.

13. A cosmetic emulsion of the composition of claim 5.

14. A cosmetic emulsion of the composition of claim 6.

15. A cosmetic emulsion of the composition of claim 18.

16. A cosmetic emulsion of the composition of claim 7.

17. A cosmetic emulsion of the composition of claim 8.

18. The composition of claim 4 where the acid moiety of said ester is that of acetic acid.

* * * * *